United States Patent [19]

Mehra

[11] Patent Number: 5,224,350
[45] Date of Patent: Jul. 6, 1993

[54] PROCESS FOR RECOVERING HELIUM FROM A GAS STREAM

[75] Inventor: Yuv R. Mehra, The Woodlands, Tex.

[73] Assignee: Advanced Extraction Technologies, Inc., Houston, Tex.

[21] Appl. No.: 881,250

[22] Filed: May 11, 1992

[51] Int. Cl.⁵ .................................................. F25J 3/00
[52] U.S. Cl. ................................................ 62/17; 55/16; 55/68; 62/20
[58] Field of Search ..................... 62/17, 20; 55/16, 28

[56] References Cited

U.S. PATENT DOCUMENTS

| | | | |
|---|---|---|---|
| 3,599,438 | 8/1971 | Blackwell et al. | 62/22 |
| 3,616,602 | 11/1971 | Hays et al. | 55/66 |
| 3,653,220 | 4/1972 | Foster et al. | 62/22 |
| 3,683,589 | 8/1972 | Seitz et al. | 55/62 |
| 4,192,661 | 3/1980 | Johnson | 62/12 |
| 4,238,211 | 12/1980 | Stuart | 62/20 |
| 4,623,371 | 11/1986 | Mehra | 62/17 |
| 4,659,351 | 4/1987 | Stuber et al. | 62/18 |
| 4,666,468 | 5/1987 | Wu | 55/16 |
| 4,666,481 | 5/1987 | Olson, Jr. | 62/11 |
| 4,690,695 | 9/1987 | Doshi | 55/16 |
| 4,701,187 | 10/1987 | Choe et al. | 55/58 |
| 4,701,200 | 10/1987 | Fisher et al. | 62/27 |
| 4,717,407 | 1/1988 | Choe et al. | 62/18 |
| 4,793,841 | 12/1988 | Burr | 62/20 |
| 4,832,718 | 5/1989 | Mehra | 62/17 |
| 4,883,514 | 11/1989 | Mehra | 62/20 |
| 4,883,515 | 11/1989 | Mehra et al. | 62/17 |

OTHER PUBLICATIONS

"Comparison of the Mehra Process for Nitrogen Rejection to a Cryogenic Process for Nitrogen Rejection from Subquality Natural Gas", Report GRI-90/-290, Gas Research Institute.

*Primary Examiner*—Ronald C. Capossela
*Attorney, Agent, or Firm*—Depaoli & O'Brien

[57] ABSTRACT

A subquality nitrogen-rich natural gas stream containing more than 0.1 mol % helium is countercurrently extracted with a lean physical solvent to produce a rich solvent bottoms stream which is flashed twice to produce a methane-rich gas product and a nitrogen-helium product which is fed to at least one membrane unit. A reject nitrogen stream and a crude helium stream are discharged from this unit. The crude helium stream is either compressed to a pressure within the range of 200 to 3,000 psia for sale or is compressed to no more than 1,000 psia and fed to a PSA unit which produces a reject nitrogen stream and a highly purified (99.99+ mol %) helium stream which is compressed to a pressure within the range of 200 to 3,000 psia for sale.

16 Claims, 1 Drawing Sheet

PROCESS FOR RECOVERING HELIUM FROM A GAS STREAM

BACKGROUND OF THE INVENTION

1. Field of the Invention

This invention relates to recovering helium from gas streams obtained from natural gas reservoirs containing minor amounts of helium, major amounts of hydrocarbons, and significant quantities of nitrogen, by utilizing the Mehra process for initial purification of the gas streams.

2. Review of the Prior Art

A significant amount of helium is often found in natural gas reservoirs, but the natural gas is frequently contaminated with fairly large amounts of nitrogen which may have originated naturally or may have been injected into the reservoirs in suitable formations, such as in the central and north Texas areas of the United States, as part of an enhanced oil recovery operation or an enhanced gas recovery operation.

Such contamination by nitrogen and helium, if present, has caused the oil producer to curtail oil production because government regulations prevent him from burning the nitrogen-rich associated gas, and both environmental laws and a desire to preserve valuable resources prohibit him from venting the associated hydrocarbons. The oil producer is thus limited by the choice of technology available to him for properly processing the associated gases from an oil well. Most prior art technology, which involves cryogenic principles, cannot economically process the natural gas streams which contain more than 3 mol % nitrogen, even after subsidization with the revenue from oil production.

U.S. Pat. Nos. 4,623,371, 4,832,718, and 4,883,514 disclose several extractive-flashing embodiments of the Mehra process for countercurrently contacting a nitrogen-rich feed gas stream, which may range from lean to rich in hydrocarbons content, at any pressure with a lean physical solvent, using an extractor column, at least one flashing stage, and optionally a regenerator column, to produce a methane-rich gas product, meeting the pipeline specification for nitrogen content, and a nitrogen product. Any helium that is present in the natural gas is in the nitrogen product and is similarly concentrated.

In March 1991, the Gas Research Institute issued Report GRI-90/0290, entitled "Comparison of the Mehra Process for Nitrogen Rejection to a Cryogenic Process for Nitrogen Rejection from Subquality Natural Gas". In this report, GRI confirmed the technical feasibility and economic benefits of the Mehra concept which operates under non-cryogenic temperatures and requires inexpensive carbon steel metallurgy. The Mehra process requires 45% less compression and 30% less energy overall and also requires 12% less capital than a comparable cryogenic process.

For many years, the helium has been extracted from helium-containing natural gas by cooling the gas stream in a cryogenic nitrogen rejection unit (NRU) to a temperature below the liquefaction points of its hydrocarbon constituents but above the liquefaction point of helium. Because both helium and nitrogen are highly volatile, helium tends to become concentrated in nitrogen recovery streams, such as in the nitrogen stream when nitrogen and methane are separated. The resulting product of this separation is called crude helium and generally comprises about 50–70% helium and 50–30% nitrogen. This crude helium is either stored for future use or is further purified to a marketable grade (99.995% purity).

Helium has been used for years as a lighter-than-air material for balloons, dirigibles, and the like and has been increasingly utilized for welding because of its chemical inertness and as a coolant for superconductivity applications.

Helium has conventionally been recovered and purified by stand-alone cryogenic processes, such as described in U.S. Pat. No. 3,599,438. Because cryogenic processes are costly, however, they have frequently been combined with adsorption processes, such as those described in U.S. Pat. Nos. 3,653,220, 4,192,661, and 4,238,211, using temperature swing adsorption, as described in U.S. Pat. Nos. 3,616,602 and 3,683,589, or pressure swing adsorption, as described in U.S. Pat. Nos. 4,659,351, 4,666,481, and 4,701,200, for regenerating the adsorbent.

Helium has also been separated from other volatile gases by permeation through thin, non-porous membranes which exhibit good selectivities for oxygen, helium, nitrogen, and carbon dioxide over other gases in gas mixtures, as described in U.S. Pat. No. 4,666,468.

In addition, U.S. Pat. No. 4,690,695 discloses the combination of one or more permeable membranes for bulk separation and for residual product gas recovery with a pressure swing adsorption (PSA) process for the recovery of high purity product gas, such as helium, the waste gas from the PSA system being passed to one or more such permeable membranes for enhanced product recovery, the recovery levels achieved being advantageously reconciled with the corresponding compression and other cost factors pertaining to the overall process for the production of such high purity product gas. Semi-permeable membrane units have been hybridized with pressure swing adsorption (PSA) units as described in U.S. Pat. No. 4,701,187 to produce purified components (99+%) at high recovery (80+%) from gas mixtures containing at least one other component because stand-alone membrane units were found to be inefficient for such high purity/high recovery products, while stand-alone adsorption units were found to be very effective in producing a purified gas stream if their feed streams were relatively pure (e.g., 70%).

U.S. Pat. No. 4,717,407 discloses a process for recovering a helium-rich stream from a helium-containing gaseous feed mixture which may be natural gas, a slip stream from a nitrogen rejection unit, or crude helium at pressures varying from atmospheric to more than 3,000 psia and at helium concentrations ranging from 0.1–90 mol %. This process recovers high-purity helium (i.e., greater than 95 mol %) and/or crude helium (i.e., 40–70 mol %).

The helium-containing gaseous feed mixture is fed to a non-membrane separation unit to produce a helium-enriched stream and a helium-depleted stream. This unit can be an adsorption, absorption, cooling, or partial condensation and/or rectification type unit. The purpose of the non-membrane unit is to alter the relative content of helium in relationship to the nitrogen content, whereby a helium-enriched stream leaves overhead, when it is an absorption unit, and a helium-diluted stream, enriched in nitrogen, leaves from the bottom of the unit.

At least a portion of the helium-enriched stream is fed to a membrane unit consisting of a cascade of membranes with an internal recycle stream, the helium-enriched stream being separated by the membranes into a helium-rich permeate stream and a helium-depleted reject stream. To obtain high-purity helium, the permeate stream is then fed to a pressure swing adsorption (PSA) unit from which a helium product of 99.99 mol % purity is obtained.

The process described in U.S. Pat. No. 4,717,407 appears not to be adapted, however, for receiving nitrogen-rich gas streams having low concentrations of helium (less than 5.0 mol %) from a nitrogen rejection unit, such as the Mehra process described in U.S. Pat. Nos. 4,623,371, 4,832,718, and 4,883,515, unless such a low-helium product stream from the nitrogen rejection unit is fed to a first membrane unit and then to a non-membrane device for further processing before final treatment in a second membrane unit, as illustrated in FIG. 4 thereof.

A need consequently exists for a method of combining the Mehra nitrogen rejection units with membrane and PSA units for producing high-purity helium from low-purity (below 5.0 mol % helium) or subquality natural gas.

SUMMARY OF THE INVENTION

The object of this invention is accordingly to provide a helium recovery process which combines the Mehra nitrogen rejection process with at least one membrane unit and a PSA unit for efficiently producing 99.99+ mol % helium from a nitrogen-rich natural gas stream containing at least 0.1 mol % helium.

The process of this invention for recovering helium from a hydrocarbon gas feed stream, containing nitrogen, at least 0.1 mol % helium, and hydrocarbons, comprises:

A. countercurrently contacting the hydrocarbon gas feed stream with a lean physical solvent selected from the group consisting of:
1) paraffinic solvents having molecular weights ranging from 70 to 140 and UOP characterization factors ranging from 12.0 to 13.5, these factors being independent of the aromatic content of said paraffinic solvents,
2) naphthenic solvents having molecular weights ranging from 70 to 130 and UOP characterization factors ranging from 10.5 to 12.0, these factors being independent of the aromatic content of said naphthenic solvents,
3) benzene, toluene, $C_8$–$C_{10}$ aromatic compounds having methyl, ethyl or propyl aliphatic groups specifically constituting a subgroup of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reformates, $C_9$ heart cuts of said reformates which are enriched in $C_9$ alkylbenzenes, $C_7$–$C_9$ alkyl aromatics, and mixtures thereof, and
4) dialkyl ethers of polyalkylene glycol, N-methyl pyrollidone, dimethylformamide, propylene carbonate, sulfolene, and glycol triacetate, to produce an overhead stream which contains at least nitrogen and helium and a hydrocarbons-rich solvent bottoms stream;

B. flashing the solvent bottom stream at least twice to produce a methane-rich gas product and a lean solvent stream, the first overhead flashed gas stream being compressed and recycled to the contacting of step A;

C. cooling and recycling the lean solvent stream to the contacting of step A;

D. feeding the overhead stream to at least one membrane unit to produce a reject nitrogen stream, which is not recycled to the contacting of step A, and a permeate helium-rich stream which contains at least 50 mol % helium; and E. compressing the permeate stream to a pressure ranging from 200 to 3,000 psia. The lean physical solvent may be a lean oil selected from the group consisting of paraffinic, naphthenic, and aromatic hydrocarbons and mixtures thereof having molecular weights ranging between about 70 and 250.

Alternatively, this permeate stream may be compressed to no more than 1,000 psia and then fed to an adsorption unit which is preferably of the pressure swing adsorption (PSA) type for recovery of its highly pure helium product (99.99+ mol %) and for regeneration of its adsorbent. However, the temperature-swing and the vacuum-swing adsorption types may also be used for regeneration of the adsorbent. This pure helium product may be compressed to a pressure ranging from 200 to 3,000 psia for storage and/or sale.

The membranes useful in this invention can be of any form known to the art, such as a homogeneous membrane, a composite membrane, or an asymmetric membrane, and may be fabricated by any known process into flat sheet membranes or spiral wound membranes wherein the sheets are prepared by extrusion, compression molding, blow molding, casting from solutions or dispersions, melt casting, and the like, or may be melt spun into tubular or hollow fiber form membranes.

Membranes made from selected polymers, such as those disclosed in U.S. Pat. No. 4,666,468, are useful and are preferably selected for maximum helium permeability. The lithium and sodium exchanged perfluorosulfonic acid polymers are particularly satisfactory.

BRIEF DESCRIPTION OF THE DRAWING

The FIGURE is a schematic flow sheet for contacting a nitrogen-rich and helium-containing gas stream with a lean physical solvent stream to produce a nitrogen-helium gas stream and a methane-rich gas product stream after at least two flashing stages, the nitrogen-helium gas stream being separated through permeable membranes into a nitrogen reject stream and a helium permeate stream which is purified in a PSA unit to produce a highly purified helium stream as product.

DESCRIPTION OF THE PREFERRED EMBODIMENT

Figure 1:
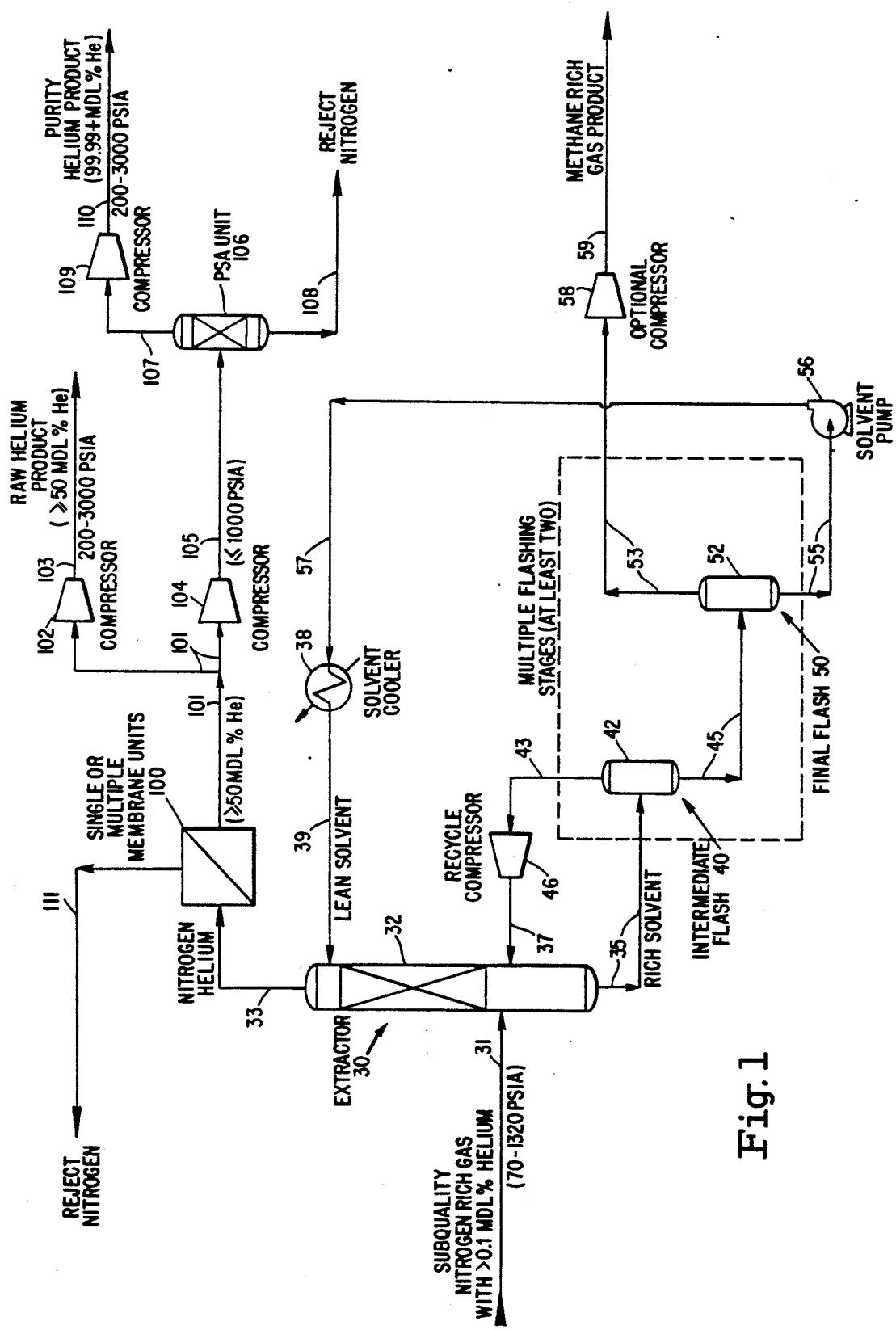

The process of this invention, as shown in the FIGURE, comprises feeding subquality nitrogen-rich gas, containing more than 0.1 mol % helium and at pressures within the range of 70 to 1,320 psia, as stream 31 to nitrogen extractor column 32, in which a liquid stream of lean solvent flows countercurrently to an ascending stream of gas, of nitrogen extractor unit 30 to produce a rich bottom solvent stream 35 of rich solvent and an overhead stream 33 of nitrogen and helium. Stream 35 is fed to flash vessel 42 of intermediate flash unit 40 to produce solvent stream 45 as bottoms and overhead stream 43 of flashed gas which is compressed to the pressure of column 32 in recycle compressor 46 and fed to the bottom of column 32 as stream 37.

Stream 45 is fed to final flash vessel 52 of final flash unit 50 to produce bottoms stream 55 of lean solvent, which is pumped by pump 56 to solvent cooler 38 and fed as stream 39 to the top of column 32, and overhead flashed stream 53 which is compressed in compressor 58, if needed, and discharged as methane-rich gas product stream 59.

Nitrogen-helium stream 33 is fed to single or multiple membrane units 100 which produce permeate helium stream 101 and reject nitrogen stream 111 which is discharged. Membrane unit 100 recovers at least 85% of the contained helium in stream 33. Stream 101 contains at least 50 mol % helium and is useful as crude helium which may be compressed in compressor 102 and discharged as raw helium product 103.

Alternatively, stream 101 may be compressed by compressor 104 to a pressure of no more than 1,000 psia and fed as stream 105 to PSA unit 106 which produces reject nitrogen stream 108 and recovers at least 85% of helium present in stream 101 as highly pure helium product stream 107 which is compressed by compressor 109 and discharged as product stream 110 at 200–3,000 psia, having a purity of 99.99+ mol % helium.

helium-rich stream 101, 103 which is 1.9% of the feed stream. The helium content of stream 101 is 89.5% of the helium in feed stream 31.

Stream 101 is then fed to a PSA unit 106 to produce highly pure stream 110 which is 99.996 mol % helium, amounting to 82.3% of the helium in feed stream 31 and 92.0% of the helium in feed stream 101.

The flow rates in pound moles per hour (lbmols/hr) and the mol percentages for the components of seven of the streams in the FIGURE are given in the following Table. It is evident that recycling of Stream 111 from membrane unit 100 to the contacting step in column 32 is not needed, so that stream 111 can be injected into the gas-producing formation, or can be used for other purposes such as fuel.

Because it will be readily apparent to those skilled in the art of separating and recovering components of hydrocarbon gases that innumerable variations, modifications, applications, and extensions of the example and the principles hereinbefore set forth can be made without departing from the the spirit and scope of the invention, what is hereby defined as such scope and is desired to be protected should be measured, and the invention should be limited, only by the following claims.

OVERALL MATERIAL BALANCE
HELIUM RECOVERY & PURIFICATION EXAMPLE

| | STREAM NUMBER | | | | | | | |
|---|---|---|---|---|---|---|---|---|
| | 31 | | 59 | | 33 | | 111 | |
| Component | Lbmole/hr | mol % | Lbmole/hr | mol % | Lbmole/hr | mol % | Lbmole/hr | mol % |
| Helium | 10.85 | 1.76% | 0.01 | 0.00% | 10.84 | 4.36% | 1.13 | 0.48% |
| Nitrogen | 219.68 | 35.65% | 9.96 | 2.71% | 209.73 | 84.44% | 207.98 | 87.94% |
| CO2 | 4.97 | 0.81% | 4.74 | 1.29% | 0.23 | 0.09% | 0.09 | 0.04% |
| Methane | 330.78 | 53.67% | 309.12 | 84.02% | 21.66 | 8.72% | 21.39 | 9.05% |
| Ethane | 35.97 | 5.84% | 33.14 | 9.01% | 2.83 | 1.14% | 2.82 | 1.19% |
| Propane | 11.96 | 1.94% | 9.83 | 2.67% | 2.14 | 0.86% | 2.14 | 0.90% |
| i-Butane | 0.56 | 0.09% | 0.37 | 0.10% | 0.19 | 0.08% | 0.19 | 0.08% |
| n-Butane | 1.24 | 0.20% | 0.69 | 0.19% | 0.55 | 0.22% | 0.55 | 0.23% |
| i-Pentane | 0.08 | 0.01% | 0.02 | 0.00% | 0.07 | 0.03% | 0.07 | 0.03% |
| n-Pentane | 0.10 | 0.02% | 0.01 | 0.00% | 0.09 | 0.03% | 0.09 | 0.04% |
| n-Hexane | 0.09 | 0.01% | 0.01 | 0.00% | 0.07 | 0.03% | 0.07 | 0.03% |
| Total | 616.29 | 100.00% | 367.90 | 100.00% | 248.39 | 100.00% | 236.52 | 100.00% |

| | STREAM NUMBER | | | | | |
|---|---|---|---|---|---|---|
| | 101 | | 110 | | 108 | |
| Component | Lbmole/hr | mol % | Lbmole/hr | mol % | Lbmole/hr | mol % |
| Helium | 9.71 | 81.80% | 8.93 | 99.996% | 0.78 | 26.45% |
| Nitrogen | 1.74 | 14.70% | 0.00 | 0.004% | 1.74 | 59.40% |
| CO2 | 0.14 | 1.20% | 0.00 | 0.00% | 0.14 | 4.85% |
| Methane | 0.26 | 2.20% | 0.00 | 0.00% | 0.26 | 8.89% |
| Ethane | 0.01 | 0.08% | 0.00 | 0.00% | 0.01 | 0.32% |
| Propane | 0.00 | 0.01% | 0.00 | 0.00% | 0.00 | 0.04% |
| i-Butane | 0.00 | 0.01% | 0.00 | 0.00% | 0.00 | 0.03% |
| n-Butane | 0.00 | 0.00% | 0.00 | 0.00% | 0.00 | 0.01% |
| i-Pentane | 0.00 | 0.00% | 0.00 | 0.00% | 0.00 | 0.00% |
| n-Pentane | 0.00 | 0.00% | 0.00 | 0.00% | 0.00 | 0.00% |
| n-Hexane | 0.00 | 0.00% | 0.00 | 0.00% | 0.00 | 0.00% |
| Total | 11.87 | 100.00% | 8.93 | 100.00% | 2.94 | 100.00% |

EXAMPLE

A subquality feed stream of natural gas, containing 1.76 mol % of helium and 35.65 mol % of nitrogen and flowing at 616.29 pound moles per hour (lbmols/hr), requires further processing before it can be fed to a pipeline. It is accordingly fed to extractor column 32, which is operated as disclosed in one or more of the following Mehra patents: U.S. Pat. Nos. 4,623,371, 4,832,718, and 4,883,515, and is then fed to at least one membrane unit 100, as shown in the FIGURE, to obtain, on a pound mole basis, a useful natural gas stream 59 which is 59.7% of the feed stream, a nitrogen reject stream 111 which is 38.4% of the feed stream, and a

What is claimed is:

1. In a process for separating $C_1+$ hydrocarbons and nitrogen from a nitrogen-rich gas stream containing at least 3 mol % of said nitrogen and at least 0.1 mol % helium, comprising the following steps:

A. contacting said nitrogen-rich gas stream with a lean oil selected from the group consisting of paraffinic, naphthenic, and aromatic hydrocarbons and mixtures thereof having molecular weights ranging between about 70 and 250, at temperatures no lower than −40° F. and pressures ranging between 70 and 1,320 psia to produce a nitrogen enriched stream containing said helium as an overhead product and a bottoms stream of methane-rich oil;

B. flashing said bottoms methane-rich oil stream to recover a methane-rich overhead gas product and a lean oil-rich bottoms stream;

C. recycling said lean-oil rich bottoms stream to said contacting of step A;

the improvement comprising recovering at least 85% of said helium by:

1) separating in a single or multistage membrane unit with internal recycles said nitrogen enriched stream of step A into a permeated low pressure raw helium product stream containing at least 50 mol % helium and a high pressure nitrogen reject stream, and 2) compressing said low pressure raw helium product stream to pressures ranging from 200 to 3,000 psia.

2. The improved process of claim 1, wherein said compressed raw helium product is at pressures less than 1,000 psia and is further separated in a pressure swing adsorption (PSA) unit to recover at least 85% of helium present in said raw helium product to produce (1) a pure helium product stream containing at least 99.99 mol % helium at a pressure similar to PSA feed pressure, and (2) a low pressure reject stream of nitrogen.

3. The improved process of claim 2, wherein said pure helium product is compressed to pressures ranging from 200 to 3,000 psia.

4. A process for recovering helium from a hydrocarbon gas feed stream, containing nitrogen, at least 0.1 mol % helium, and hydrocarbons, which comprises:

A. countercurrently contacting said hydrocarbon gas feed stream with a lean physical solvent selected from the group consisting of:

1) paraffinic solvents having molecular weights ranging from 70 to 140 and UOP characterization factors ranging from 12.0 to 13.5, said factors being independent of the aromatic content of said paraffinic solvents, 2) naphthenic solvents having molecular weights ranging from 70 to 130 and UOP characterization factors ranging from 10.5 to 12.0, said factors being independent of the aromatic content of said naphthenic solvents, 3) aromatic solvents selected from the group consisting of benzene, toluene, $C_8$–$C_{10}$ aromatic compounds having methyl, ethyl or propyl aliphatic groups specifically constituting a subgroup of o-xylene, m-xylene, pxylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reformates, $C_9$ heart cuts of said reformates which are enriched in $C_9$ alkylbenzenes, $C_7$–$C_9$ alkyl aromatics, and mixtures thereof, and 4) dialkyl ethers of polyalkylene glycol, N-methyl pyrollidone, dimethylformamide, propylene carbonate, sulfolene, and glycol triacetate, to produce an overhead stream which contains at least nitrogen and helium and a hydrocarbons-rich solvent bottom stream;

B. flashing said solvent bottom stream at least twice to produce a methane-rich gas product and a lean solvent stream, the first overhead flashed gas stream being compressed and recycled to said contacting of said step A;

C. cooling and recycling said lean solvent stream to said contacting of said step A;

D. feeding said overhead stream of said step A to at least one membrane unit to produce a reject nitrogen stream and a permeate helium-rich stream which contains at least 50 mol % helium; and E. compressing said permeate stream to a pressure ranging from 200 to 3,000 psia.

5. The process of claim 4, wherein said permeate stream is compressed to no more than 1,000 psia and is then fed to an adsorption unit for recovery of its highly pure helium product.

6. The process of claim 5, wherein said helium product is at least about 99.99+ mol % pure.

7. The process of claim 5, wherein pressure swinging is used for regeneration of adsorbent in said adsorption unit.

8. The process of claim 5, wherein temperature swinging is used for regeneration of adsorbent in said adsorption unit.

9. The process of claim 5, wherein vacuum swinging is used for regeneration of adsorbent in said adsorption unit.

10. The process of claim 6, wherein said highly pure helium product is compressed to a pressure ranging from 200 to 3,000 psia for storage and/or sale thereof.

11. A process for separating $C_1+$ hydrocarbons and nitrogen from a nitrogen-rich gas stream containing at least 3 mol % of said nitrogen and at least 0.1 mol % of helium, comprising the following steps:

A. contacting said nitrogen-rich gas stream with a lean oil selected from the group consisting of paraffinic, naphthenic, and aromatic hydrocarbons and mixtures thereof having molecular weights ranging between about 70 and 250, at temperatures no lower than −40° F. and pressures ranging between 70 and 1,320 psia, to produce a nitrogen enriched stream, in which the ratio of said helium to said nitrogen is essentially unchanged, as an overhead product and a methane-rich oil stream as a bottom product;

B. flashing said bottom methane-rich oil stream to recover a methane-rich overhead gas product and a lean oil-rich bottom stream;

C. recycling said lean-oil rich bottom stream to said contacting of step A;

D. feeding said nitrogen enriched stream produced in step A to a membrane unit comprising at least one thin, nonporous membrane exhibiting good selectivity for helium over nitrogen and methane and therein separating said nitrogen enriched stream into a low-pressure helium product as a permeate stream containing at least 50 mol % helium and a high-pressure nitrogen reject stream which is not recycled to said contacting of said step A; and E. compressing said permeate stream to pressures ranging from 200 to 3,000 psia.

12. The process of claim 11, wherein said permeate stream is compressed to pressures less than 1,000 psia and is then fed to a pressure swing adsorption (PSA) unit and therein separated into a pure helium product stream containing at least 99.99 mol % helium at pressures similar to PSA feed pressure and a low-pressure reject stream of nitrogen which is not recycled to any other of said units.

13. The process of claim 12, wherein said pure helium product stream is compressed to pressures ranging from 200 to 3,000 psia.

14. The improved process of claim 11, wherein said paraffinic hydrocarbons are selected from the group consisting of paraffinic solvents having molecular weights ranging from 70 to 140 and UOP characterization factors ranging from 12.0 to 13.5, said factors being independent of the aromatic content of said paraffinic solvents.

15. The improved process of claim 11, wherein said naphthenic hydrocarbons are selected from the group consisting of naphthenic solvents having molecular weights ranging from 70 to 130 and UOP characterization factors ranging from 10.5 to 12.0, said factors being independent of the aromatic content of said naphthenic solvents.

16. The improved process of claim 11, wherein said aromatic hydrocarbons are selected from the group consisting of benzene, toluene, $C_8$–$C_{10}$ aromatic compounds having methyl, ethyl or propyl aliphatic groups specifically constituting a subgroup of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reformates, $C_9$ heart cuts of said reformates which are enriched in $C_9$ alkylbenzenes, $C_7$–$C_9$ alkyl aromatics, and mixtures thereof.

* * * * *